(12) United States Patent
Jelinek

(10) Patent No.: US 8,050,468 B2
(45) Date of Patent: Nov. 1, 2011

(54) FINGERPRINT ACQUISITION SYSTEM

(75) Inventor: Jan Jelinek, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 910 days.

(21) Appl. No.: 12/042,929

(22) Filed: Mar. 5, 2008

(65) Prior Publication Data
US 2009/0226054 A1    Sep. 10, 2009

(51) Int. Cl.
*G06K 5/00* (2006.01)
(52) U.S. Cl. ............ 382/125; 382/126; 355/77; 355/22; 600/509; 600/549
(58) Field of Classification Search .................. 382/125, 382/126; 600/509, 549; 355/77, 22
See application file for complete search history.

(56) References Cited

U.S. PATENT DOCUMENTS

| 5,689,576 | A | 11/1997 | Schneider et al. |
| 6,377,700 | B1 | 4/2002 | Mack et al. |
| 6,751,344 | B1 * | 6/2004 | Grumbine ..................... 382/154 |
| 7,162,075 | B2 | 1/2007 | Littlefield et al. |
| 7,257,714 | B1 | 8/2007 | Shen |
| 7,397,943 | B2 | 7/2008 | Merbach et al. |
| 2006/0023197 | A1 * | 2/2006 | Joel ................................. 355/77 |
| 2006/0233427 | A1 | 10/2006 | Hauke et al. |

FOREIGN PATENT DOCUMENTS

| DE | 10153808 | 5/2003 |
| DE | 20121729 | 6/2003 |
| EP | 1187055 | 7/2007 |
| JP | 2001273497 | 10/2001 |
| WO | 2008154589 | 12/2008 |

* cited by examiner

*Primary Examiner* — Mike Rahmjoo
(74) *Attorney, Agent, or Firm* — Seager, Tufte & Wickhem LLC

(57) ABSTRACT

An acquisition system for obtaining images of a fingerprint from a finger, or marks of another kind of target. The system may have two or more cameras positioned at different directions towards the target. Each camera may have a light source for illuminating the target from a direction different than that of the respective camera. The cameras may take sequences of images of the target at different focuses as the whole target might not be in focus in one image due to a depth of focus being less than the depth of the target. Portions of the images showing the target in focus may be cut from the images and stitched together to result in an image revealing virtually the whole target in focus. This target may be a fingerprint to be rolled out on or in a two dimensional medium for analysis, identification, storage, and so on.

12 Claims, 3 Drawing Sheets

FINGERPRINT ACQUISITION SYSTEM

BACKGROUND

The present invention pertains to obtaining images and particularly to acquisition images of items.

SUMMARY

The invention is a system for standoff object capture and appropriate image replication of, for instance, a fingerprint.

DESCRIPTION

Figure 1:
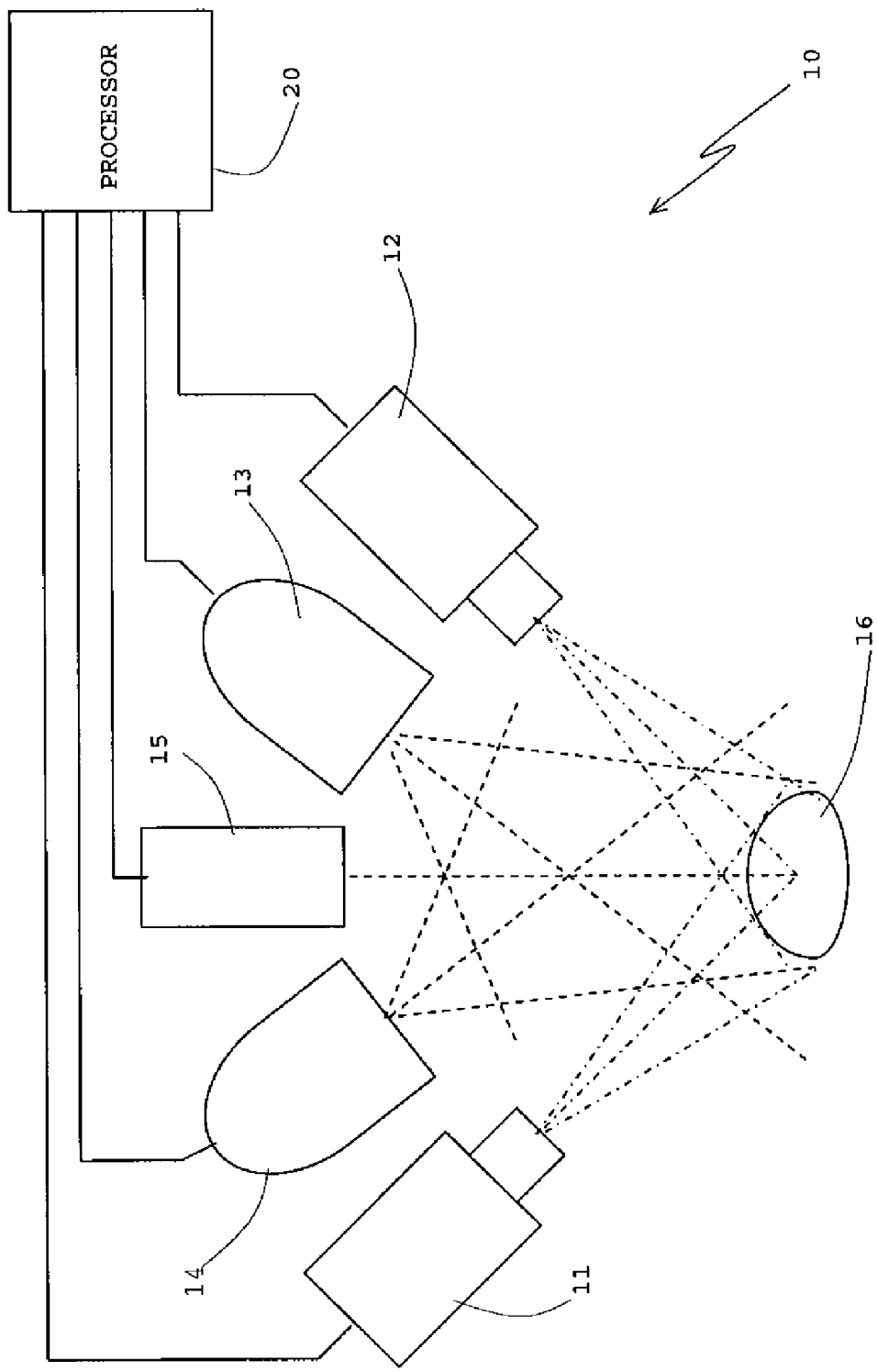
FIG. 1 is a diagram of an apparatus for fingerprint standoff acquisition.

The present invention is a system which may enable a standoff capture of the so called "roll finger" kind of fingerprints. The system may overcome various issues common with the existing fingerprint collection methods. First, it seems be difficult to achieve consistent fingerprint quality since good finger printing may depend on the experience of an officer doing the fingerprinting. Without the need for an officer to manually roll the subject's finger over a paper card or sensor pad, this source of quality inconsistency may be eliminated. Further, because of the subject's extensive involvement and cooperation required in the traditional fingerprinting process, an experienced subject may game the system, i.e., prevent the officer from obtaining a fingerprint of adequate quality. Next, the related-art fingerprinting approaches appear labor and time intensive and thus unsuitable for mass processing facilities like immigration checkpoints at airports. Also, the related-art approaches may require physical contact with the fingerprinting device and thus could pose a serious hygienic hazard at mass processing facilities unless they are continuously monitored to assure sanitary conditions.

The present fingerprint acquisition system may operate using light from the visible spectrum to acquire the images within a certain range of distances. It may use affordable optics for the device to work from a few to few tens of centimeters in field of focus depth. A cooperative subject may have to show one or more fingers within a defined volume of space of the system. The system would not necessarily have other constraints. In particular, the subject need not touch any sensor or other part of the acquisition system.

According to an FBI standard, a roll image of a fingerprint should capture at least 80 percent of the finger bulb surface arc. Since the bulb has high curvature, one needs a panoramic picture or image of the bulb. The system may use two or possibly more images, taken from different vantage points, which are then stitched together into the single panoramic image. This stitching process may be assisted by special markers which the system projects onto the finger.

An aspect is how the system may cope with the limited depth of field of the camera optics. Practical considerations may lead to lens designs whose depth of field is a fraction of a millimeter. Since the finger bulb has an arc profile, having a depth dimension as large as 10 mm or so; there appears to be no way that a single image can be in focus uniformly over the entire finger bulb surface. Such image might only be constructed synthetically from a sequence or series of images whose focus lens positions sweep in succession the whole depth of the finger bulb surface.

An aspect of photographic fingerprint acquisition may concern an unfolding of a synthetic panoramic image of a fingerprint, which has depth information associated with each of its local patches and thus is, in effect, three-dimensional made into a two-dimensional planar fingerprint image. To accomplish the latter, traditional non-photographic approaches may require the subject being fingerprinted to roll the finger over a paper card from one nail edge to the other. To obtain a fingerprint, and an image similar to the fingerprint, the image may be achieved by unfolding the panoramic image with software using the depth information collected as a side effect of the system to cope with the limited depth of field of the camera's optics.

The present fingerprint acquisition system may conform to the FBI's IAFIS Electronic Biometric Transmission Specification (EBTS) standard, particularly the IAFIS-DOC-01078-8.001 document dated Oct. 24, 2007, at triple "w" dot fbibiospecs.org/fbibiometric/docs/EBTS%20V8.001%2010-24-07.pdf. Appendix F of the EBTS standard may indicate technical parameters that a fingerprint scanner and its images should meet in order to be certifiable by the FBI for biometric fingerprint acquisition. The standard appears to be primarily concerned with the contact-requiring scanner technologies and thus some parameters may need to be adapted for contactless scanners.

One parameter of the FBI standard may deal with is the present system's field of view. In Table F-1, the EBTS standard defines preferred capture sizes for various kinds of fingerprints used by the FBI. Generally, these sizes may fall into two categories, roll and plain images. The former images may be more difficult to acquire by a standoff device, because they are two-dimensional renditions of what actually is a three dimensional surface of the finger's last link bulb. In addition to the visual information, the system should develop the notion of the image depth; otherwise the system cannot necessarily "roll out" the data flat with the high geometric accuracy as indicated by the EBTS standard. In order to economize on resources, one may limit the system's scope to the roll images only. However, the system may be used for plain images.

A roll finger image may have the width and height of about 1.6 inches and 1.5 inches, respectively. Other dimensions may be prescribed. In order not to impose unusual requirements on the subject's cooperation, a device's field of view should include a margin of an inch or so, on the sides. Another parameter of the EBTS standard may indicate that the roll image should cover at least 80 percent of the full roll arc length, which may be defined as an arc length from nail edge to nail edge.

The EBTS standard may recognize two image formats having image point densities set at 500 and 1000 ppi, respectively. By itself, the standard may be concerned about the output image format and not the number of pixels that a camera sensor should have in order to meet the desired fingerprint image quality in terms of details to be discernible in it. The pixel density in an object plane (i.e., at the finger surface, not at the sensor, which lies in the image plane of the camera lens) may be determined from the modulation or contrast transfer function parameters in the Tables F-2 or F-3, using an optimal sampling theorem. An informal calculation shows that one may need about 15 and 25 pixels/mm for the 500 and 1000 ppi images, respectively, to achieve about a 50 percent contrast. At those densities, the sensor should have at least 615×570 and 1025×950 pixels, respectively, to accommodate the preferred roll finger area. While easily feasible if one restricts the field of view to the finger alone, adding a margin to allow some finger placement flexibility may quickly increase the sensor size. For example, a camera using a 1280×1024 pixel sensor (i.e., a 1.3 megapixel camera) may provide 22 mm on either side of the finger horizontally and 15 mm vertically for the 500 ppi image. Cameras for implementing the 1000 ppi format may also be readily available.

The full gamut of possible fingerprints listed in the Table F-1 may be pursued. A camera having a 16 megapixel sensor may barely suffice to cover the full palm with its size of 5.5 by 8 inches, with no pixels left to spare for the margin. However, a possibly more expensive camera having a 24.8 megapixel sensor may have pixels to spare for adequate margins. Such sensor may be available from Sony Corporation. Sensors having more pixels and/or greater frame rates may be used in the system. If a larger and/or faster sensor is not desired, then camera panning and tilting may be implemented to accommodate a smaller and/or slower sensor in the present system.

Once an image is formed, it may be re-sampled at 500 or 1000 ppi before it is output from the system. The camera optics may be designed to accommodate the following. Unlike the fingerprint cards, the ridges and valleys of skin pores do not necessarily have distinct reflectance as black ink and white paper do. Consequently, if they are to be seen in the image, it may be because of different angles between the surface normals of ridges and valleys, the incident light, and the camera's line of sight. A light source collocated with the camera in the perfect frontal view of the finger may make its pores (nearly) invisible. Another fact to consider is that in order to cover 80 percent of the finger arc, there should be at least two cameras.

FIG. 1 shows a system 10 having a configuration with two cameras 11 and 12. There may be more than two cameras. The two camera configuration may be used for the roll finger image capture of the fingerprint of a finger 16. Even though the two cameras 11 and 12 may be used, the images taken do not necessarily constitute a stereo pair. A more fitting description of the images may be that of a panoramic or composite picture or image of the finger 16 arc. Each camera 11 and 12 may have its own strobe light 13 and 14, respectively. Camera 11 may be supported by light source 13, which illuminates from an oblique angle the part of the finger 16 bulb that is in its field of view. Camera 12 may be supported by light source 14, which illuminates from an oblique angle the part of the finger 16 bulb that is in its field of view.

The difference of directions of cameras 11 and 12 may be greater than zero degrees. The direction of camera 11 or 12 relative to the direction of light source 13 or 14, respectively, may be greater than zero degrees. The differences of directions between the cameras may be adjusted for optimal capture of the fingerprint of the finger or other marks of a target. The difference in directions of each camera and its corresponding light source may be adjusted for optimal capture of the fingerprint of the finger or other marks of a target.

The strobe lights of sources 13 and 14 may appear necessary to freeze the finger motion during image exposure, which may be about 1 millisecond (ms) in duration. The two cameras 11 and 12 may take pictures or images one nearly immediately after the other so that the duration between the pictures or images is about 1 ms apart, making them concurrent for practical purposes. The durations may be of other values.

With the arrangement system 10 components, contrast of details in the pictures or images may, as needed, be enhanced by adjusting the angle between the directions of each respective camera and its light source. Also, the contrast of details in the pictures or images may be improved with post-processing.

Once taken, the pictures or images, or portions of them, from the respective cameras 11 and 12 may be properly stitched together. Since the subject's finger 16 might have no fixed, well defined position in space, the images of the cameras 11 and 12, respectively, may have a slightly different size, location and/or orientation in the frame, and before stitching, the images may be adjusted with a resizing, shifting and/or rotating in order for them to match up for the stitching. To aid in stitching appropriately, each image may have one or more registration marks, which are pixel-size bright spots projected onto the finger 16 by a registration mark projector 15. For instance, at 15 pixels/mm, a marker spot of a couple of pixels wide may be only about 0.1 mm in diameter and thus will not necessarily seriously affect the resulting image quality, since the spots would be comparable to pixel defects often present in sensors.

Cameras 11 and 12, lights 13 and 14, and marker 15 may be connected to a processor 20. The processor may contain software for controlling the cameras, lights and marker. It may also process and stitch camera images into a panoramic image or composite image with adjustments and the stitching resulting in an image of the whole finger 16 bulb area sufficient to meet the EBTS standard noted herein.

Considering the requirements on the resulting image quality, it appears physically impracticable to design optics that would have sufficient depth of field to produce an image of the whole finger bulb area in focus. In any image and for any feasible optics, there may nearly always be parts of the finger bulb that appear in focus and other parts not in focus. There may be parts of the bulb in the image which are measurably deteriorated, blurred and wiped out in details due to a small depth of focus. If one needs a nearly perfect image of the whole roll fingerprint, then it should be created synthetically from multiple images.

There may be wavefront coding that is designed to increase the depth of field of an optical system. However, such improvement may come at the expense of reduced spatial bandwidth of the system. The optical system may trade its minimum size of discernible detail or resolution for an increased depth of field. Given the requirements that the IAFIS standard places on the spatial resolution through its Tables F-2 and F-3, one would not necessarily be in a position to afford such a tradeoff. Yet, in some cases, both good depth of field and resolution are desired and may even be needed. Computational optics may provide a way to resolve such dilemma. For instance, a burden of gaining added depth of field may include such things as more computation.

The present system may take a sequence of images of the same object, item or target, find in each image local patches (i.e., areas) where the image appears out of focus but not corrupted, and then construct an artificial image by assembling together high quality patches extracted from the various images. First, the high quality patches may be identified, and then enough information may be acquired to assemble them together appropriately. As to the quality, the contrast over a patch may be locally measured to decide if it contains adequate details or not. As to an assembly of the patches, a sequence of images may be taken in a rapid succession such that the subject more or less remains in the same place. Then the patches having good focus may be put together like ready-to-use jigsaw puzzle pieces, without having to custom fit each patch into a final mosaic.

Figure 2:
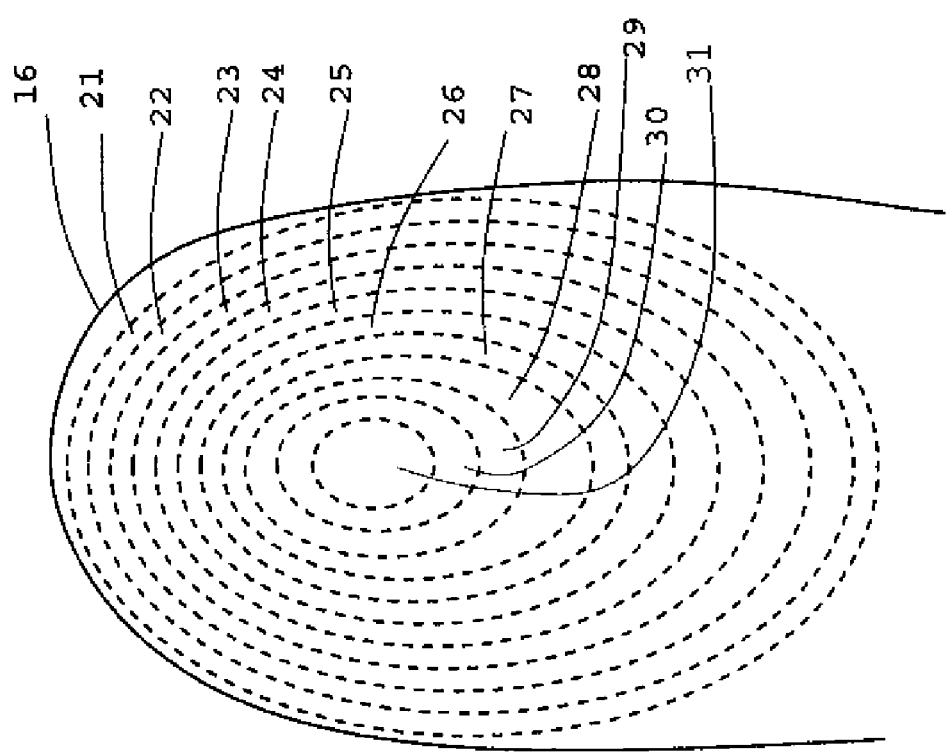
FIG. 2 is a diagram of an example map of various focused areas on a bulb of a finger.

The camera optics may have particular depth of field, for instance, 0.5 mm, at a certain focus and lens setting. If the finger bulb curves away from the camera over the 5 mm depth, then at least ten frames should be taken, from which one may obtain a nearly perfect synthetic image. The system camera may take 100 frames per second. Cameras having such rates may be available for various sensor sizes, such as those larger than 1.3 megapixels. Then the ten-frame sequence may take about 100 ms to record, which is generally a short enough time to expect the subject to hold a finger steady in one place. If it is not a sufficiently short enough time, then the images of the frames may be just slightly misregistered, a situation which appears fixable. During the frame sequence or series, the camera lens may continuously change its focus, for example, from a baseline distance of 100 mm to 99.5 mm, 99.0 mm, 98.5 mm, 98.0 mm, 97.5 mm, 97.0 mm, 96.5 mm, 96.0 mm, 95.5 mm and 95.0 mm, for each frame, respectively, to span a 5 mm depth. An example of various camera optics focus settings for a certain depth of focus may include areas 21, 22, 23, 24, 25, 26, 27, 28, 29, 30 and 31 on item or finger 16 bulb as indicated by the dashed lines shown in FIG. 2. The fingerprint of finger 16 is not shown in FIG. 2 for illustrative clarity. The areas 21-31 may be any shape and magnitude, and not necessarily as shown in the example of FIG. 2. These areas may be cut out, adjusted and stitched into a well-focused image of a full or nearly full fingerprint of finger 16, but sufficiently full or complete to meet the EBTS standard. The same approach may be used for attaining an image of a group of fingers or even the whole palm of a hand, and/or a corresponding print. Additional like sequences from one or more other cameras of system 10 may be acquired as desired or needed to contribute to forming the complete or panoramic image of item 16 or its print.

Having a very short depth of field may become an advantage rather than impediment, because it allows reconstruction of the depth dimension of a resulting image with an accuracy sufficient for rolling out a three dimensional image into a final fingerprint in or on a two dimensional planar medium.

Figure 3:
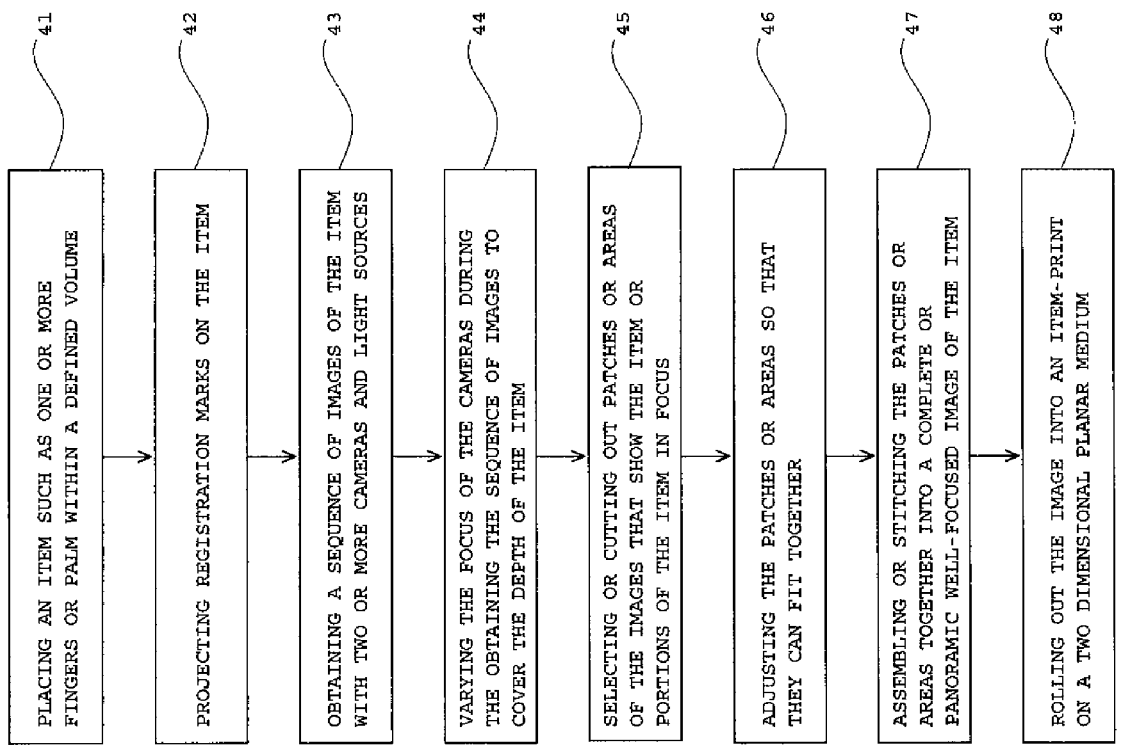
FIG. 3 is a block diagram of the present approach of fingerprint standoff acquisition.

FIG. 3 is a block diagram of an example approach for the present system 10 of FIG. 1. Blocks may have various arrangements, or some may be left out or new ones added. A block 41 may provide for placing an item such as one or more fingers or a palm within a defined volume available for capture with the image acquisition device or camera system 10. Also, illumination may be provided in this volume. Following block 41 may be a block 42 which may provide for projecting registration marks on the item with projector 15. Obtaining a sequence of images of the item with two cameras 11, 12, or more cameras and corresponding light sources 13, 14, or more, situated in different directions to capture portions and aspects, as desired or needed, of, for example, the three dimensional item 16, may follow in block 43. Also, varying the focus of the cameras during the obtaining the sequence of images to cover the depth of the item as indicated in block 44 may occur concurrent with block 43. Once the images are obtained, there may be selecting or cutting out patches or areas of the images that show the item or portions of the item in focus as noted in block 45. Block 46 indicates that there may be an adjusting of the patches or areas so that they can fit together like ready-to-use jigsaw puzzle pieces into a larger image. The latter may be followed with an assembling or stitching the patterns or areas together into a complete or panoramic well-focused image of the item or target as noted in block 47. Block 48 indicates the image of the item being rolled out into an item-print, which may be for instance a fingerprint, on a two dimensional planar medium such as a fingerprint card.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. An item acquisition system comprising:
   two or more cameras directed at a location for a target;
   one or more light sources associated with each camera and directed at the location;
   a marker directed at the location; and
   a processor connected to the cameras, the light sources and the marker; and
   wherein:
   at least two cameras have different directions relative to each other;
   each light source has a direction different than the direction of the camera with which the respective light source is associated;
   the cameras are for acquiring a series of images of a target;
   the cameras change focus during the acquiring a series of images of a target;
   some images of the series of images have areas of the target within focus;
   the areas showing the target within focus are cut out from the images; and
   the areas cut out from the images are stitched together into a focused image of much or virtually all of the target.

2. The system of claim 1, wherein:
   the target is a bulb of a finger containing a fingerprint; and
   the focused image of the target is rolled out as the fingerprint on a two-dimensional medium.

3. The system of claim 1, wherein the cameras change focus in increments approximately equal to a depth of focus through a range of focusing which approximately covers a depth of the target, during the acquiring of the series of images of the target.

4. The system of claim 3, wherein the target is a finger having a fingerprint.

5. The system of claim 4 wherein:
   an increment of depth of focus is approximately 0.5 mm; and
   the range of focusing is approximately 5 mm.

6. A method for acquiring an image of an item, comprising:
   directing two or more cameras at an item;
   directing two or more light sources at the item;
   providing illumination of the item with a light source corresponding to a capturing an image by a respective camera of the two or more cameras;
   capturing images of the item with the two or more cameras;
   combining at least portions of some of the images to provide a nearly complete and focused image of the item; and
   wherein:
   the images are captured sequentially with the two or more cameras;
   the two or more cameras have a focus which is changed while the images are captured; and
   combining at least portions of some of the images comprises:
   cutting from the images patches which have the item in focus; and resizing, shifting and/or rotating patches as needed to match the patches with adjacent patches being stitched together for providing the nearly complete and focused image of the item.

7. The method of claim 6, wherein:

registration marks are provided on the item to be in the captured images; and the registration marks are for aiding in matching the patches with other patches relative to stitching the patches together.

8. The method of claim 7, wherein:

the item is a fingerprint; and further comprising rolling out the nearly complete and focused image as a fingerprint on a two dimensional medium.

9. A standoff capture system comprising:

a first image acquisition device directed in a first direction towards a target;

a second image acquisition device directed in a second direction towards the target;

a first illuminator directed in a third direction towards the target;

a second illuminator directed in a fourth direction towards the target;

the first illuminator is for providing light for the first image acquisition device; and the second illuminator is for providing light for the second image acquisition device; and wherein:

the first and second acquisition devices are for capturing a sequence of images at various focuses of the target; and the first and second acquisition devices capture each image of a sequence at nearly the same time;

patches are selected out from the sequence of images showing portions of the target in focus; and stitching the patches together into a focused image of the target.

10. The system of claim 9, further comprising:

a projector for providing marks on the target; and wherein the first and second illuminators are strobe lights.

11. The system of claim 9, wherein:

the target is a finger; and the focused image of the target is rolled out as a fingerprint in a two dimensional medium.

12. The system of claim 9, wherein:

the first and third directions differ greater than zero degrees;

the second and fourth directions differ greater than zero degrees; and the first and second directions differ greater than zero degrees.

* * * * *